(12) United States Patent
Laczik

(10) Patent No.: US 6,545,764 B1
(45) Date of Patent: Apr. 8, 2003

(54) NON-CONTACT TOPOGRAPHICAL ANALYSIS APPARATUS AND METHOD THEREOF

(75) Inventor: Zsolt John Laczik, Oxford (GB)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 09/831,734
(22) PCT Filed: Nov. 15, 1999
(86) PCT No.: PCT/GB99/03802
§ 371 (c)(1), (2), (4) Date: Jul. 20, 2001
(87) PCT Pub. No.: WO00/29835
PCT Pub. Date: May 25, 2000

(30) Foreign Application Priority Data

Nov. 13, 1998 (GB) .............................................. 9824986

(51) Int. Cl.$^7$ .............................................. G10B 11/14
(52) U.S. Cl. ........................ 356/601; 356/625; 356/635; 356/388; 356/390
(58) Field of Search ................................ 356/600, 601, 356/614, 625, 630, 634, 635, 237.1–237.6, 390, 394, 398, 388; 250/222.1, 458.1

(56) References Cited

U.S. PATENT DOCUMENTS

| | | | | |
|---|---|---|---|---|
| 3,663,107 A | | 5/1972 | Denis et al. ................ | 356/120 |
| 4,589,773 A | * | 5/1986 | Ido et al. .................... | 356/601 |
| 5,135,309 A | * | 8/1992 | Kuchel et al. .............. | 356/601 |
| 5,194,729 A | * | 3/1993 | Okisu et al. ............. | 250/222.1 |
| 5,307,152 A | * | 4/1994 | Boehnlein et al. .......... | 356/601 |
| 5,392,110 A | * | 2/1995 | Yojima et al. .............. | 356/601 |
| 5,471,307 A | | 11/1995 | Koliopoulos et al. ....... | 356/371 |
| 5,801,824 A | | 9/1998 | Henley ....................... | 356/237 |
| 6,252,236 B1 | * | 6/2001 | Trulson et al. ........... | 250/458.1 |

FOREIGN PATENT DOCUMENTS

DE 44 08 226 A1 3/1994
WO WO 98/36240 8/1998

OTHER PUBLICATIONS

Patent Abstracts of Japan, vol. 017, No. 241 (E–1364), May 14. 1993 & JP 04 367245 A (Hitachi Ltd), Dec. 18, 1992 abstract.

Patent Abstracts of Japan, vol. 010, No. 348 (P–519), Nov. 22, 1986 & JP 61 148308 A (Mitsubishi Heavy Ind Ltd), Jul. 7, 1986 abstract.

Riesz Ferenc: "Makyoh–topography studies of mirror–like surfaces: toward a quantitative understand." PRO SPEI INT. SOC. OPT. ENG., vol. 3573, 1998, pp. 292–295, XP000874703 USA.

Laczik Zsolt John: "Quantitative Makyoh topography" PROC. SPIE INT SOC OPT ENG, vol. 3743, May 19–21, 1999, pp. 151–156, XP000874538 Bellingham WA USA.

Szabo, Janos; Riesz, Ferenc; and Szenpali, Bela: "Makyoh Topography: Curvature Measurements and Implications for the Image Formation" Jpn. J. Apl. Phys. vol. 35, No. 2b, Feb. 15, 1996 pp. L258–L261, XP000730566 paragraph 3.

* cited by examiner

Primary Examiner—Frank G. Font
Assistant Examiner—Sang H. Nguyen
(74) Attorney, Agent, or Firm—Drinker Biddle & Reath LLP (57) ABSTRACT

Topographic analysis apparatus consists of a light source (1) and associated optics (2) for illuminating a mirrored surface O with a parallel light beam. Light reflected from the mirrored surface is collected by a camera (4) that is mounted on a moveable carriage (5) so that images of the mirrored surface O may be recorded at a plurality of different distances from the surface. The Makyoh topograms produced using this apparatus are then analyzed using phase extraction software to iteratively determine the profile of the surface of the object and the object's reflectivity. In this way Makyoh topograms may be used for quantitative as well as qualitative analysis of a reflective surface such as a semiconductor wafer.

22 Claims, 6 Drawing Sheets

NON-CONTACT TOPOGRAPHICAL ANALYSIS APPARATUS AND METHOD THEREOF

FIELD OF THE INVENTION

The present invention relates to non-contact topographical analysis apparatus and a method thereof and in particular to the generation of Makyoh topograms enabling quantitative measurement of variations in the mirrored surface of an object. The present invention is particularly concerned, but not exclusively, with the simultaneous measurement of the reflectivity and height variations of a large mirror-polished surface, such as defects in semiconductor wafer surfaces.

BACKGROUND OF THE INVENTION

For the current generation of microelectronic circuits, the manufacturing process requires perfectly flat large diameter semiconductor wafers. There is a well-defined need for characterisation techniques that can accurately assess the polishing quality of these wafers and can be used as quality control and production line monitoring tools providing qualitative pass/fail type information and also as troubleshooting tools providing detailed and accurate quantitative information.

It has been known for some time that when a collimated beam of light is reflected by an approximately flat mirror-polished object and a screen is placed in the path of the reflected beam some distance away from the object, a 'mirror image' of the object is formed on the screen. For a perfectly flat object with uniform reflectivity, the light intensity in the 'mirror image' would be substantially uniform with some small variations due to edge diffraction effects close to the perimeter of the object. However, for objects with surface height variations, the 'mirror image' no longer has a uniform intensity distribution. Even small height variations in the surface of the object will show up strongly amplified as dark or bright patches/lines in the 'mirror image'. 'Mirror images' of this type are called Makyoh topograms or 'magic mirror images'. Makyoh topography has been used for a number of years as a tool for the inspection of mirror-polished surfaces, and in particular as a quality control tool for the assessment of semiconductor wafer surfaces.

Figure 1:
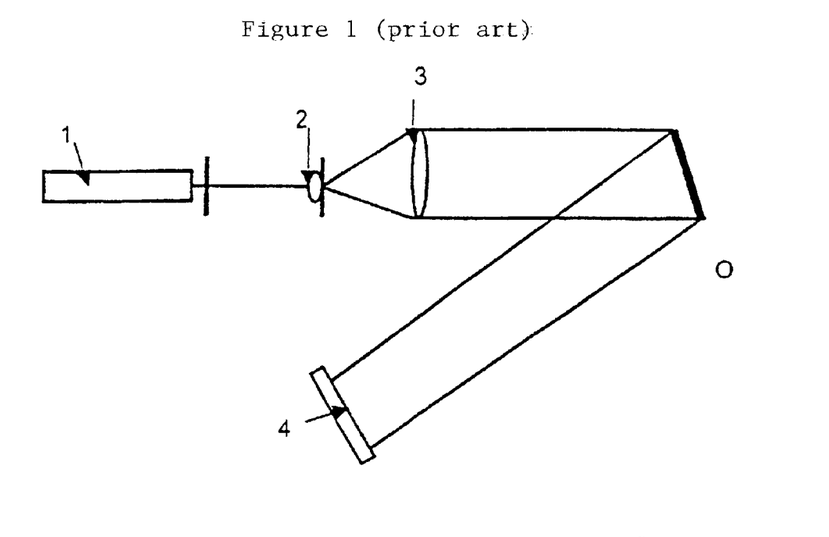
FIG. 1 is a schematic diagram of a conventional Makyoh topograph.

In FIG. 1 a conventional Makyoh topograph is shown schematically. Light from a laser 1, or a bright lamp with a narrow bandpass filter, is homogenised using a diffuser, fly's eye optics, or spatial filter assembly 2. A collimator lens 3 then forms an approximately parallel light beam, which in turn is reflected by the object 0 under test. The reflected beam is intersected either by a screen 4 for direct viewing or by a film or electronic camera for image recording. The object-camera distance is fixed and normally is in the range of 0.5 m to 2 m.

Figure 2A:
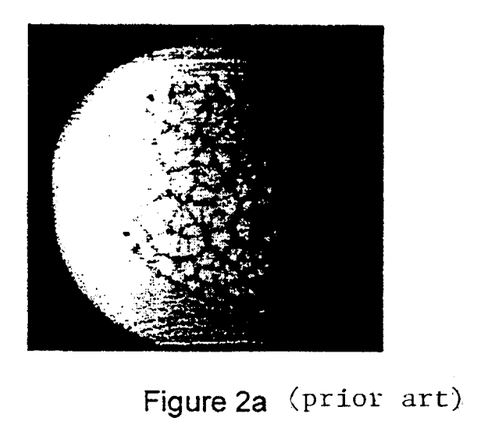
FIGS. 2a. 2b and 2c are conventional Makyoh topograms from three different mirror-polished InP wafers.
Figure 2B:
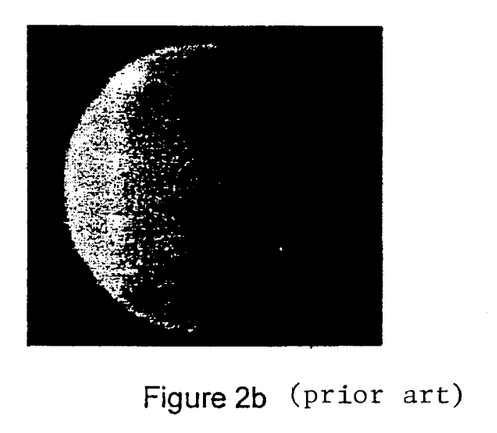
Figure 2C:
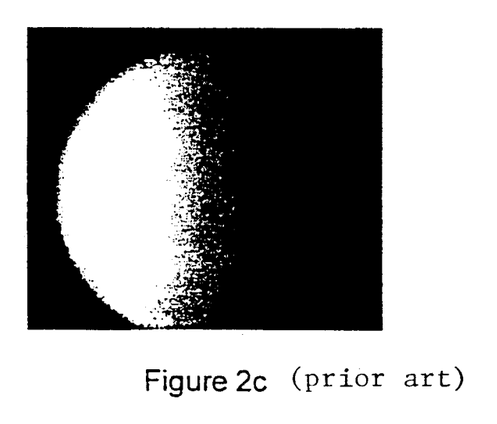

Typical Makyoh topograms from three different mirror-polished InP wafers are shown in FIGS. 2a, 2b and 2c. In FIG. 2a the image contrast is rather complex with the following main components: curved approximately parallel lines probably corresponding to saw or lapping marks; concentric circles in the centre of the image probably corresponding to growth striation lines; dark lines with cellular geometry probably corresponding to surface ridges caused by uneven mounting wax distribution during polishing; and dark and bright spots probably corresponding to mounds and dimples respectively. The wafer shown in FIG. 2b is of better overall quality, the only features revealed in the topogram are concentric circles in the centre and a small number of bright spots at random positions. Finally, the wafer shown in FIG. 2c is of excellent quality only exhibiting some very faint low contrast lines and spots. These images provide a qualitative measure of wafer polishing quality, however it is not possible to extract the actual height of the ridge network revealed in FIG. 2a or the depth of the dimples in FIG. 2b. As demonstrated by these images, conventional Makyoh topograms can be a very powerful tool for qualitative comparison, but they provide no quantitative information and the interpretation of the image contrast can be very complicated.

U.S. Pat. No. 4,547,073 describes apparatus for generating Makyoh topograms that includes a convex lens for converging light reflected from the object in order to project a defocussed image on the screen. With the apparatus described in U.S. Pat. No. 4,547,073 the distance between the object and the screen is reduced, in comparison to apparatus that does not employ a convex lens thereby making the apparatus more convenient for industrial use. A geometrical optics explanation is provided as to how the variations in surface height result in changes in intensity in the mirror image. However, the explanation is very general relying as it does on equating variations in surface height solely to a concave/convex mirror effect. This document provides no assistance as to how a quantitative analysis of the Makyoh topograms might be achieved.

The main drawbacks of Makyoh topography as described above are: Ambiguity in the interpretation of the topograms: almost identical Makyoh topograms can result from an object with some given surface height profile and constant reflectivity; an object with constant surface height and a given non-uniform reflective or an object with both height variations and a non-uniform reflectivity profile.
Lack of quantitative interpretation of the topograms.

SUMMARY OF THE INVENTION

The present invention seeks to provide improved topographical analysis apparatus and a method thereof that at least improves and in many cases overcomes the disadvantages described above with conventional Makyoh topography and in particular enables a quantitative interpretation of Makyoh topograms generated with the present invention.

The present invention provides a topographical analysis method for measuring variations in reflectivity or surface height of a reflective object comprising: illuminating a reflective surface of the object with a beam of light; recording with a recording device a plurality of images of the surface of the object generated by light reflected from the surface in which each image has a predetermined optical transformation with respect to every other image; measuring the light intensity distribution in each of the images generated by the reflected light; and determining and outputting at least one of the reflectivity and the relative surface height of the reflective surface of the object by predicting the reflectivity and relative surface height of an initial theoretical surface, iteratively adjusting the theoretical surface until the calculated light intensity distributions for the theoretical surface, corresponding to the optical transformations of each of the recorded images, converge with the recorded images.

Preferably the theoretical surface is adjusted by cyclical substitution of the calculated image intensity for the theoretical surface with the detected image intensity of each one of the images generated by the reflected light. In the preferred embodiment the light distribution of the theoretical surface is deemed to have converged when the difference between the calculated image intensity and the detected image intensities is less than a predetermined threshold.

In one embodiment of the present invention the plurality of images are recorded each at a different distance from the reflective surface of the object. The recording device may be moved to different positions along the optical axis of the reflected light to sequentially record the plurality of images. Alternatively, the reflected light may be divided into a plurality of portions with each portion of the reflected light being directed to a separate recording device in which the path length from the reflected surface of the object to each recording device is different. In a further alternative the effective path length between the object and the recording device may be altered by adjusting any optical elements located between the object and the recording device.

In a further or alternative embodiment the image generated by the reflected light is recorded at a plurality of different, distinct wavelengths. Additional optical elements may be provided for modifying (e.g. collimating) the incident beam of light. Where such additional elements are provided, the elements may be adjustable to enable the plurality of images each with a different optical transformation to be generated.

In a second aspect the present invention provides topographical analysis apparatus for measuring variations in the reflectivity or surface height of a reflective object comprising an optical system for directing a beam of light to a reflective surface of the object; a first recording device for recording a first image of the surface of the object generated by light reflected from the surface; at least one further recording device for recording one or more further images of the surface of the object, thereby generating a plurality of images in which each image has a predetermined optical transformation with respect to every other image: and an analyser for measuring the light intensity distribution in each of the plurality of images and for determining and outputting at least one of the reflectivity and the relative surface height of the reflective surface of the object by iteratively adjusting a theoretical surface, having an initial predetermined reflectivity and surface height, until the calculated light intensity distributions for the theoretical surface, corresponding to the optical transformations of each of the recorded images, converge with the recorded images.

Ideally, the analyser further includes a thresholding device for monitoring the difference between the calculated image intensity of the theoretical surface and the recorded image intensities and for determining that the theoretical surface substantially corresponds to the surface of the reflective object when the difference is less than a predetermined value.

The light source may be one or more narrow band-width sources such as lasers etc. Also, the first and the one or more further recording devices may be electronic cameras.

In one embodiment the first recording device and the one or more further recording devices is a single camera mounted on a moveable support for positioning the camera at different distances from the reflective surface of the object.

In a further or alternative embodiment the first and one or more further detector devices are wavelength specific and each is sensitive to a different distinct wavelength.

In a further aspect the present invention provides phase extraction software on a data carrier for determining variations in reflectivity or surface height of a reflective object, the software being programmed to perform the following steps: storing the measured light intensity distributions of a plurality of images of a reflective object in which each image has a predetermined optical transformation with respect to every other image; predicting the reflectivity and relative surface height of an initial theoretical surface and calculating the light intensity distribution for the theoretical surface; and iteratively adjusting the theoretical surface until the calculated light intensity distributions for the adjusted theoretical surface, corresponding to optical transformations of the stored images, converge with the stored light intensity distributions.

With the present invention, optical apparatus is provided for the recordal of more than one Makyoh topogram from the same object. The topograms are generated in such a way that the light intensity distributions resulting in the different topograms are subject to well-defined and different optical transformations (e.g. phase dispersion) on travelling from the object to the recording device. The quantitative interpretation of a set of such topograms then becomes a phase retrieval problem that can be solved using iterative numerical algorithms. With the present invention iterative Fourier transform techniques are employed that, where possible, are used to obtain a unique solution for the object reflectivity and surface height (phase) distributions.

Embodiments of the present invention will now be described, by way of example, with reference to the accompanying drawings, in which:

DETAILED DESCRIPTION OF THE DRAWINGS

As mentioned above conventional Makyoh topographs and their explanation in terms of geometrical optics fails to provide any quantitative measure of the variations in surface height. In order to determine the exact values of intensity as a function of lateral position, diffraction effects have to be taken into account. In the paraxial, coherent regime (which is a valid approximation for the optical systems considered here) the following simplified treatment can be employed. For the light beam reflected by the mirror and for an axial position immediately next to it, the complex amplitude distribution $\alpha_m(x,y)$ can be calculated by applying an operator P to the mirror reflectivity $r(x,y)$ and the mirror surface height $h(x,y)$, i.e. $\alpha_m(x,y)=P\{r(x,y),h(x,y)\}$. In this notation the operator P is a function of the wavelength $\lambda$ and the wavefront $\alpha_0(x,y)$ incident on the mirror. If $\alpha_0$ is a constant plane wave with magnitude $u_0$ and wavelength $\lambda$ and the mirror surface is smooth, $\alpha_m=P\{r,h\}$ takes the simple form of:

$$\alpha_m = u_0 r(x,y) e^{-i2\pi h(x,y)\lambda}$$

Here the wavefront tilt caused by the non-perpendicular angle of incidence was ignored; this however does not effect the generality of the treatment. The complex amplitude distribution $\alpha_{i(xi,y_i)}$ at the camera can then be calculated by applying the free-space phase dispersion operator to $\alpha_m$. In the Fourier domain this takes the form $F\{\alpha_i\}=HF\{\alpha_m\}$. For the geometry considered here, H is a multiplication by the factor $$e^{-i\pi\lambda z(f_x^2-f_y^2)}$$

where z is the distance between the mirror-polished surface and the camera and $f_x$ and $f_y$ are the Fourier-space co-ordinates, giving for $\alpha_i$ the expression:

$$a_i = F^{-1}\left\{e^{-i\pi\lambda z(f_x^2+f_y^2)} F\{u_0 r(x,y) e^{-i2\pi h(x,y)/\lambda}\}\right\}. \qquad (1)$$

The image intensity $I_i$ can then be calculated by taking the square modulus of $\alpha_i$, i.e. $I_i=|\alpha_i|^2$.

Figure 3A:
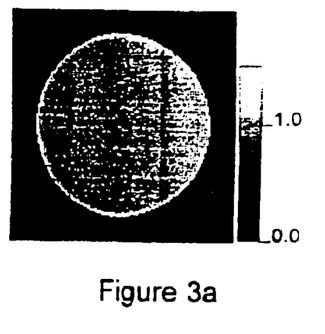
FIGS. 3a and 3b are diagrams of a test object surface in which the reflectivity (FIG. 3a) is constant but the phase (FIG. 3b) varies by virtue of four surface dimples.
Figure 3B:
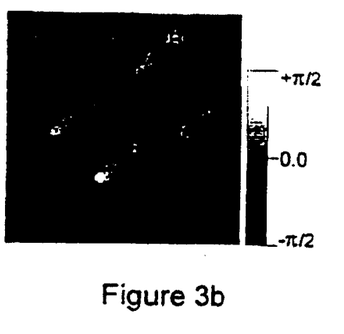

As proof of the validity of the above equation, a test mirror object (FIGS. 3a and 3b) was assumed with constant r=1.0 reflectivity (FIG. 3a) and a flat surface with four dimples 1/100, 1/50, 1/20 and 1/10 λ deep (marked A, B, C and D respectively in FIG. 3b). The phase is inversely proportional to the object surface height and so the dimples A, B, C and D are shown as bright spots in FIG. 3b. Using the analysis set out above, two Makyoh images were calculated for the test object for object-to-screen distances of z=1 m (FIG. 4a) and z=2 m (FIG. 4b). The similarity between these calculated images and actual Makyoh topograms produced using conventional topographs is remarkable and confirms the validity of this approach to a quantitative measurement of Makyoh topograms.

If the illumination were incoherent the above results would not be valid, however a similar treatment could easily be developed and applied as necessary.

In order to make Makyoh topography quantitative the functions $r(x,y)$ and $h(x,y)$ would need to be recovered from a measured $I_i(x_i,y_i)$. If the phase of Makyoh images was available, the process represented by Eq. (1) could be inverted and the object reflectivity and phase (height) could be recovered. However, since only intensity can be measured. the phase information is lost. On the basis of a single Makyoh topogram Eq.(1) cannot be inverted and a unique quantitative solution for $r(x.y)$ and $h(x,y)$ cannot be obtained.

As mentioned above, this problem is a phase retrieval problem that arises when trying to determine $r(x,y)$ and $h(x,y)$ from intensity measurements. Using the topograhical analysis method and apparatus and associated phase extraction software described below. at least two separate images generated by the reflected light are recorded and the light intensity distribution of the images measured. A theoretical surface with a predetermined reflectivity and surface height profile is assumed and using phase retrieval software is iteratively adjusted. using the algorithm set out below, so that the calculated image intensities of the theoretical surface converge on the recorded image intensities under the same parameters. Once the differences between the calculated image intensities and the recorded image intensities are less than a threshold value. the theoretical surface is deemed to be an accurate representation of the actual surface under study. An explanation of how such an iterative approach is implemented in practice is set out below.

Eq. (1) for the complex image amplitude can be presented in the following general form:

$$\alpha_i = F^{-1}HFP\{r(x,y) h(x,y)\} \qquad (2)$$

where P is a function of the illumination complex amplitude $\alpha_0$ and the wavelength $\lambda$ and H is a function of the distance z between the object and the camera and the wavelength $\lambda$. Applying the inverse of Eq. (2) to $\alpha_i$, r and h can be found as $$r(x,y) = F^{-1}H^{1}FP_r^{-1}\{\alpha_i\}$$

and $$h(x,y) = F^{-1}H^{1}FP_h^{-1}\{\alpha_i\}.$$

The notation can be simplified by defining a composite operator C as $$C = F^{-1}HFP,$$

$$C_r^{-1} = F^1 H^1 FP_r^{-1} \text{ and}$$

$$C_h^{-1} = F^1 H^1 FP_h^{-1}.$$

With this notation the algorithm described above can be applied in the retrieval of phase information from a Makyoh topogram in the following manner.

Two Makyoh topograms $I_A$ and $I_B$ are recorded under two different sets of imaging conditions having corresponding complex amplitudes $\alpha_A$ and $\alpha_B$, and imaging operators $C_A$ and $C_B$. Using the method described above for the retrieval of phase information from a pair of images, the first iteration is performed with an arbitrary phase assumed for $\alpha_A$:

$$a_{B,1} = \sqrt{I_B} \, e^{i \arg(C_B\{C_{A,r}^{-1}\{\sqrt{I_A}\, e^{i\phi\Omega}\}C_{A,h}^{-1}\{\sqrt{I_A}\, e^{i\phi\Omega}\}\})} \text{ and}$$

$$a_{A,1} = \sqrt{I_A} \, e^{i \arg(C_A\{C_{B,r}^{-1}\{a_{B,1}\}C_{B,h}^{-1}\{a_{B,1}\}\})}.$$

The process is then repeated with values from the previous iteration, $$a_{B,n+1} = \sqrt{I_B} \, e^{i \arg(C_B\{C_{A,r}^{-1}\{a_{A,n}\}C_{A,h}^{-1}\{a_{A,n}\}\})}.$$

$$a_{A,n+1} = \sqrt{I_A} \, e^{i \arg(C_A\{C_{B,r}^{-1}\{a_{B,n+1}\}C_{B,h}^{-1}\{a_{B,n+1}\}\})}.$$

until changes in $A_i$ and $A_p$ become smaller than a given pre-set limits or thresholds. Once sufficient convergence is achieved, object reflectivity and height can be calculated from either $\alpha_A$ or $\alpha_B$.

If the illumination or image forming optical paths included additional optical elements (e.g. lenses) or a somewhat modified geometry was used, the actual form of C and $C^{-1}$ would be different. However, the general argument and the algorithm described above would still be applicable if a) the two measured images $I_A$ and $I_B$ possessed sufficient reciprocity for the algorithm to converge, b) the inverse operator $H^{-1}$ existed and c) the inverse operator $P^{-1}$ existed and was separable in rand h.

Figure 4A:
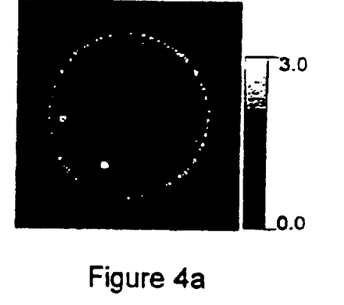
FIGS. 4a and 4b are diagrams of the calculated Makyoh topograms generated for the test object of FIGS. 3a and 3b at an object/camera separation of 1m (FIG. 4a) and 2m (FIG. 4b)
Figure 4B:
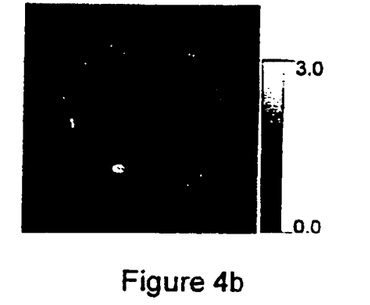
Figure 5A:
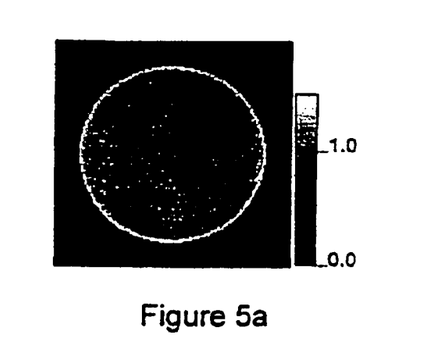
FIGS. 5a and 5b are diagrams of the reflectivity and phase respectively of a reconstructed object surface based on the topograms of FIGS. 4a and 4b.
Figure 5B:
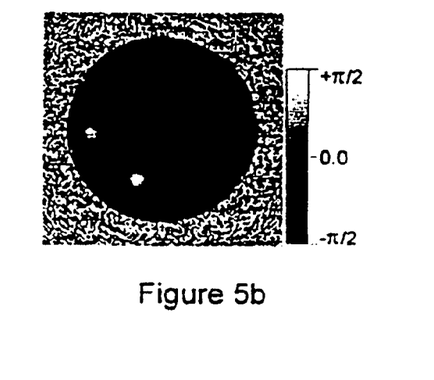
Figure 6A:
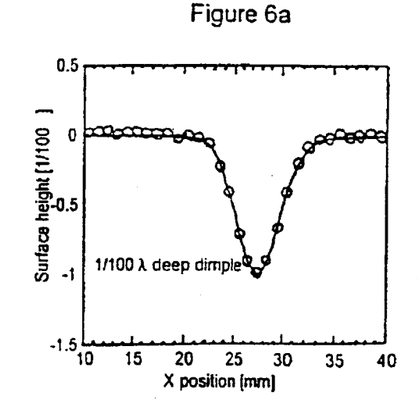
FIGS. 6a, 6b, 6c and 6d are line traces taken from the surfaces of FIGS. 3a, 3b, 5a and 5b that run respectively through the four reconstructed dimples.
Figure 6B:
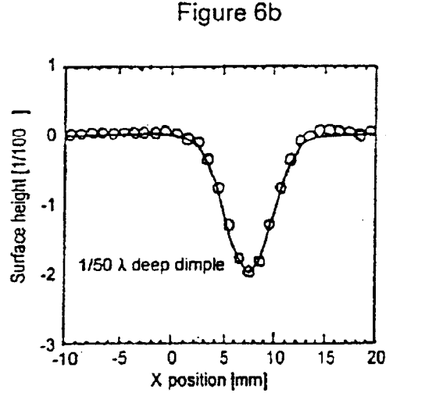
Figure 6C:
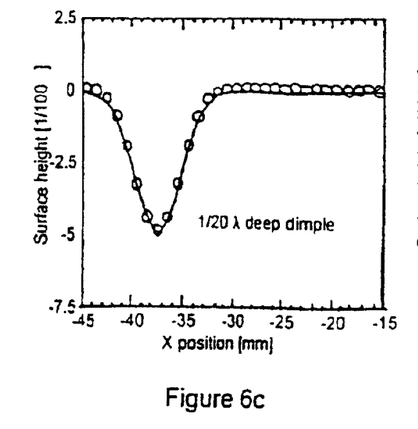
Figure 6D:
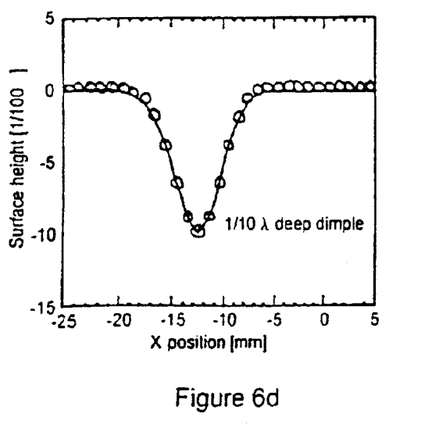

To test the phase retrieval software described above, it was applied to the topograms shown in FIGS. 4a and 4b. The results of the reconstruction are shown in FIGS. 5a and 5b (c.f. the original object is shown in FIGS. 3a and 3b). FIG. 5a shows the reconstructed reflectivity which is constant and FIG. 5b shows the reconstructed phase (height) which varies in the form of four dimples that differ in height. The agreement between the reconstruction and the original test image is further illustrated by the line traces shown in FIGS. 6a, 6b, 6c and 6d. The traces were selected such that they go through the centre of the dimples in the surface of the test object shown in FIGS. 3a and 3b. The solid line in the line traces correspond to the original surface and the circles represent data points for the reconstructed surface height profile.

Thus, to enable quantitative measurement of the mirror-polished surface of an object, two or more independent mirror images of the object with sufficient reciprocity are required. This condition will be satisfied if one or more of the corresponding constituent pairs of the operator pair $C_A/C_B$, i.e. $H_A/H_B$ and $P_A/P_B$, are sufficiently different. In addition the geometry of the optical arrangement has to ensure the existence of the inverse operators required by the reconstruction algorithm referred to above.

Figure 7:
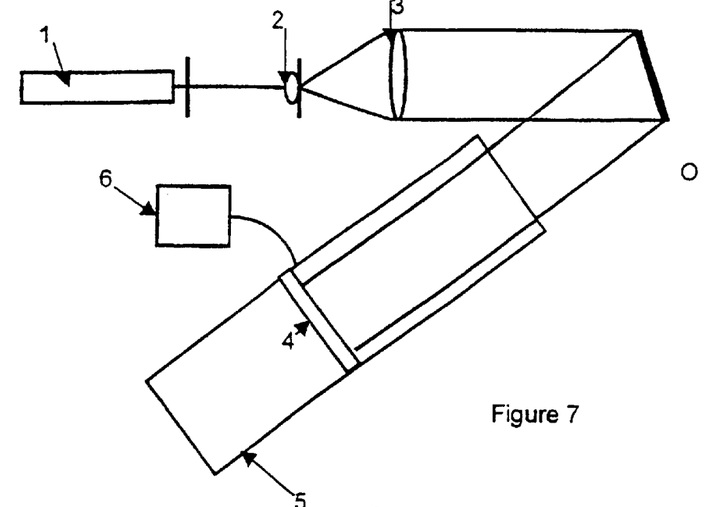
FIG. 7 is a schematic diagram of a topographical analysis apparatus in accordance with the present invention.

Topographical analysis apparatus capable of providing a quantitative as well as a qualitative measure of variations in reflectivity and phase (surface height) of a mirror-polished object, employing the method set out above is shown in FIG. 7. Many of the features of this apparatus also appear in the conventional Makyoh topograph shown in FIG. 1 and where appropriate the same reference numerals are employed.

The topographical analysis apparatus includes a light source 1 such as a laser or a bright lamp with a narrow band-pass filter for illuminating the mirror-polished surface of an object O. The light from the light source 1 passes through an optical system that homogenises the light and generates a parallel light beam. The optical system may conveniently consist of a diffuser, fly's eye optics or spatial filter assembly 3 and a collimator lens. Preferably, the parallel light beam has a cross-section sufficiently large to illuminate the entire surface of the object. Alternatively, only a portion of the surface of the object may be illuminated in which case different parts of the object can be illuminated in turn to enable a complete image of the surface of the object to be constructed from the individual mirror-images produced using the topographical analysis apparatus.

Light reflected from the surface of the object is intersected by a camera 4 so that the mirror image can be analysed. The camera may use film or may be electronic with a pixellated image frame. The camera 4 is mounted on a moveable support 5 such as a trolley or carriage in moving engagement with guide rails (not shown). The moveable mount 5 is arranged for movement parallel to the reflected light beam so that the camera 4 may be moved to two or more different positions at different distances z from the object. At each of the two or more positions a separate mirror image of the surface of the object is generated so that the quantitative information can be extracted from the plurality of mirror images. Instead of continuously variable positions, a plurality of positions of the moveable mount 5 may be predetermined. The camera 4 is connected to an analyser that implements the algorithm set out above for the extraction of both reflectivity and surface height quantitative data.

Figure 8:
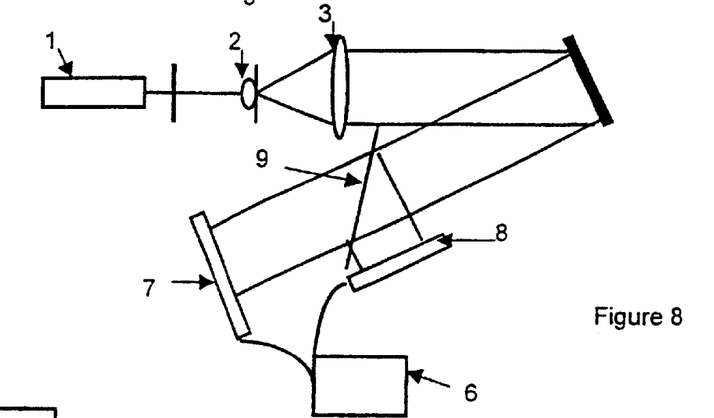
FIG. 8 is a schematic diagram of alternative topographical analysis apparatus in accordance with the present invention.

As shown in FIG. 8, instead of the camera 4 having a moveable mount 5, a plurality of fixed cameras 7, 8 may be employed in combination with a beam splitter 9 inserted in the path of the reflected light beam. The plurality of cameras are each positioned to provide different fixed z values. This arrangement has the advantage that simultaneous recording of a plurality of mirror images by the cameras can be achieved and the images supplied to the analyser 6. In a further alternative, if the object-to-screen optical path includes additional optical elements, say lenses, similar effects on H can be achieved by mounting one or more of the optical elements on a moveable support.

With each of the embodiments given above, as H is a function of z, different $H_A$, $H_B$, ... operators can be obtained for each camera position. Assuming the operators to be sufficiently different, the reconstruction algorithm can be employed by the analyser 6 to iteratively extract phase information from the plurality of substantially independent mirror images.

Instead of varying the object to camera distance z, the complex amplitude distribution of illumination may be varied to again produce a plurality of substantially independent mirror images. This can most conveniently be achieved by mounting the collimator lens 3 on a moveable support (not shown) so that the collimator lens 3 may be moved to different positions along the optic axis. In this way different $P_A$, $P_B$, ... operators can be obtained.

Figure 9:
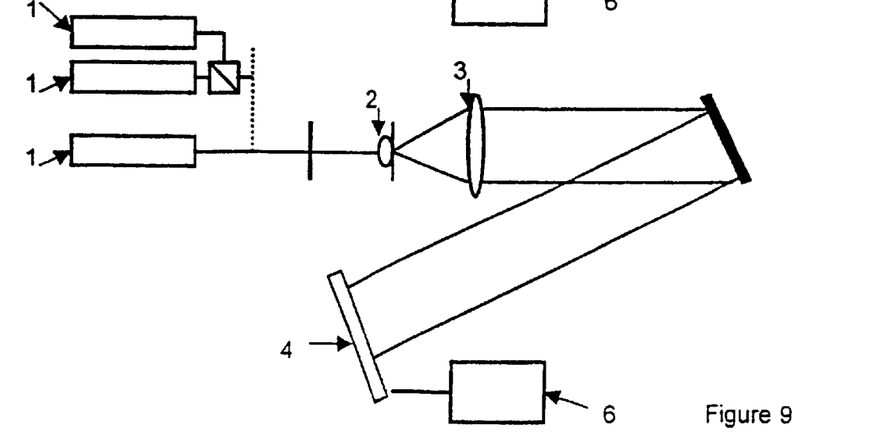
FIG. 9 is a schematic diagram of a third embodiment of topographical analysis apparatus in accordance with the present invention.

Since both H and P are functions of the illumination wavelength $\lambda$, if provisions are made for illumination at two or more wavelengths and for independent image recording at those wavelengths (for example by means of a colour camera) different $C_A$, $C_B$, ... operators can be obtained. An example for this type of system is shown in FIG. 9. The topographic analysis apparatus includes, as for the previous embodiments, a spatial filter 2 and a collimator lens 3 for directing a parallel beam of light onto the surface of the object O. A camera 4 is positioned in the optic axis of the reflected light to produce a mirror image of the object surface. The camera 4 may be a conventional film or digital camera, capable of recording images at a broad range of wavelengths. In which case the beam of light incident on the object is wavelength specific and one or more further mirror images are successively generated each at a different wavelength. To ensure the incident beam of light is wavelength specific, the light source may be a tuneable narrow band laser or alternatively a plurality of lasers each generating light at different frequencies that are sequentially aligned with the optical axis of the apparatus.

If a colour specific camera is employed, then the object may be illuminated with light at a plurality of distinct wavelengths and a plurality of successive mirror images may again be obtained at the different wavelengths. Of course, a beam splitter may be employed in the manner shown in FIG. 8 to enable two mirror images at different wavelengths to be generated simultaneously.

In addition, any combination of the above arrangements may also be used. For example, a plurality of images can be recorded at different wavelengths and at different positions by combining the arrangements of FIGS. 7 and 9.

The apparatus in FIG. 9 is preferred as both H and P are varied. Also, where more than two independent mirror images are generated, the robustness and convergence speed of the reconstruction algorithm may be significantly improved.

Figure 10:
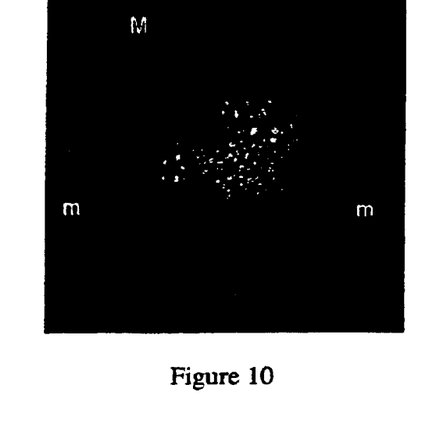
FIG. 10 is a Makyoh topogram of a sample InP wafer.
Figure 11:
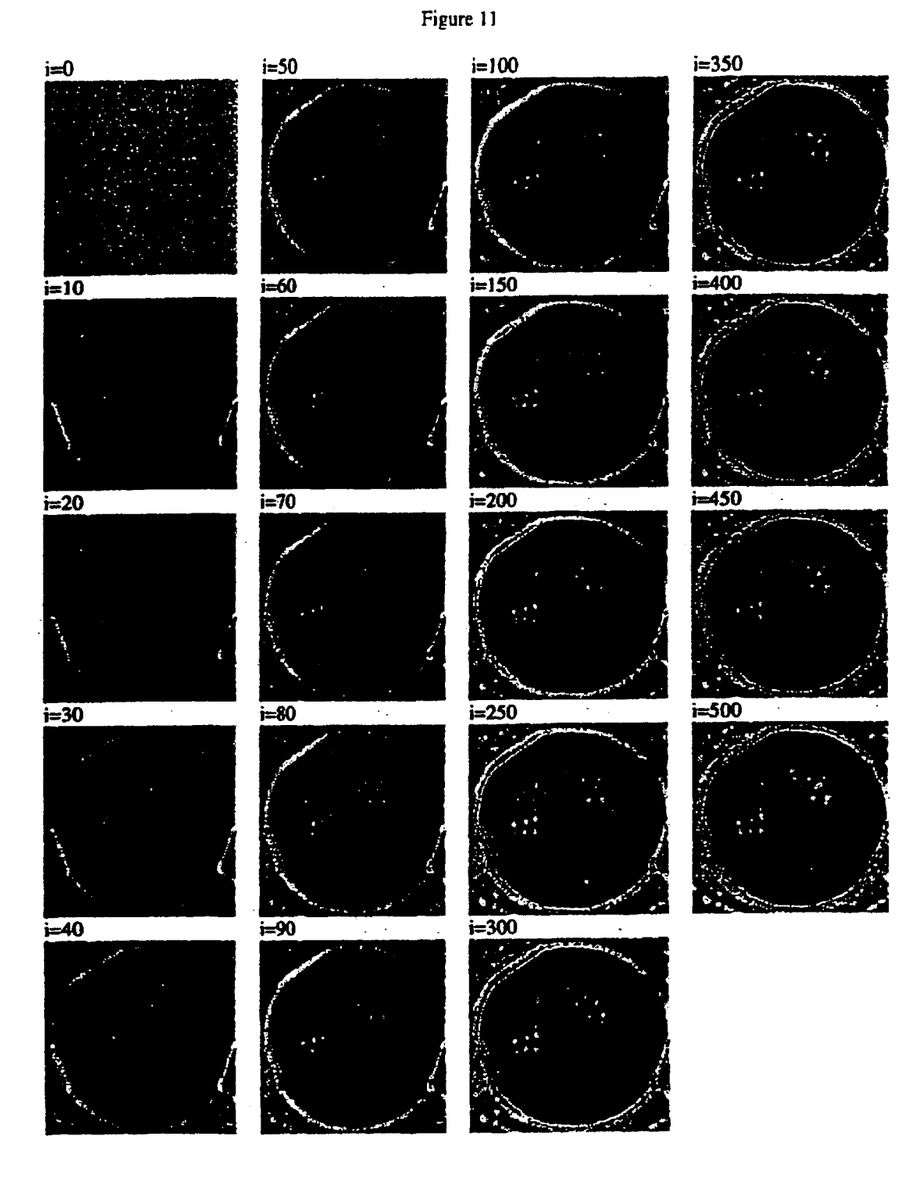
FIG. 11 is a series of reconstructed Makyoh topograms converging on the topogram of FIG. 10.
Figure 12:
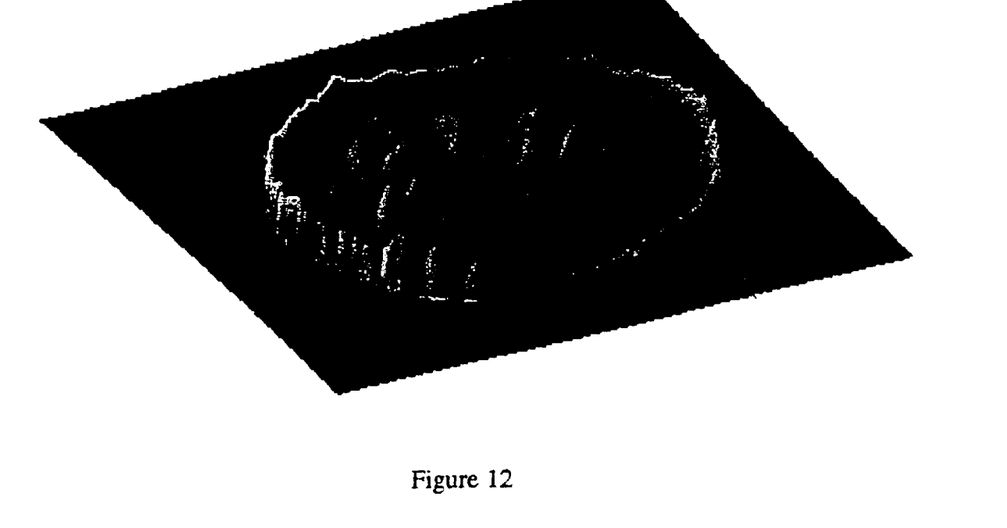
FIG. 12 is a three dimension diagram of the calculated surface profile of the surface of the wafer of FIG. 10.

The apparatus shown in FIG. 7 was used to take a series of Makyoh topograms of a sample semiconductor wafer, one of which is shown in FIG. 10. The dark regions marked m indicate where the mounting wedges for holding the wafer are positioned. The sample was a polished 50 mm diameter InP wafer and the topogram of FIG. 10 was recorded at an image to object distance of 656.6 mm. Additional topograms were recorded closer to the object. The image contrast is complex consisting of concentric circles in the center of the wafer, irregular large dark and bright patches and a pronounced cellular network of dark lines with bright spots in the centre region of the cells. The phase extraction software described above was applied starting with an initial random image phase (i=0). After only approximately 100 iterations (i=100) the rate of change for the reconstructed images decreased significantly and finally the process was stopped after 300 iterations when no further changes were observed even in the fine detail of the reconstructed images. From the measured intensities of the reconstructed topogram phases the object reflectivity and phase shift were then calculated. The object reflectivity was found to be close to unity for the whole wafer but the object was found to introduce significant phase shifts. Having reconstructed the phase shift, reconstruction of the object height profile was straightforward.

The present invention provides a number of advantages over the conventional Makyoh topography. Firstly, interpretation of the recorded topograms is unambiguous and provides quantitative data with high sensitivity. Also, both object reflectivity and height measurements are provided. Moreover, the topographic apparatus is simple in construction and affords a wider range of applicability when compared to conventional Makyoh topography. It will of course be apparent that the phase extraction software may be used separately from the apparatus described above where appropriate Makyoh topograms of a reflective object are provided for analysis.

The simplicity of the topographic apparatus makes it suitable for retrofitting to existing conventional systems. For example a beam splitter and a second camera at a different height can be added to an existing Makyoh topograph. Alternatively, a beam splitter and a second camera can be used in combination with mirrors to lengthen the optical path of a portion of the reflected light. Indeed, all of the embodiments described above can be implemented with existing conventional apparatus.

Although reference has been made herein to the use of the present invention to quantitatively measure the mirror-polished surface of a wafer, it will be appreciated that the present invention may be employed in many different situation where near perfect mirror surfaces are required. For example, the invention may be used to monitor the quality of mirrors used in communications and with lasers.

What is claimed is:

1. A topographical analysis method for measuring variations in reflectivity or surface height of a reflective object comprising:
    illuminating a reflective surface of the object with a beam of light;
    recording with a recording device a plurality of images of the surface of the object generated by light reflected from the surface in which each image has a predetermined optical transformation with respect to every other image;
    measuring the light intensity distribution in each of the images generated by the reflected light; and
    determining and outputting at least one of the reflectivity and the relative surface height of the reflective surface of the object by predicting the reflectivity and relative surface height of an initial theoretical surface, iteratively adjusting the theoretical surface until the calculated light intensity distributions for the theoretical surface, corresponding to the optical transformations of each of the recorded images, converge with the recorded images.

2. A method as claimed in claim 1, wherein the theoretical surface is adjusted by substitution of the calculated image intensity for the theoretical surface with the detected image intensity of one of the images generated by the reflected light.

3. A method as claimed in claim 2, wherein the detected image intensity of each of the plurality of images is sequentially substituted for the calculated image intensity of the theoretical surface.

4. A method as claimed in claim 3, wherein the light intensity distribution of the theoretical surface is deemed to have converged when the difference between the calculated image intensity and the detected image intensities is less than a predetermined threshold.

5. A method as claimed in claim 1 wherein the plurality of images are recorded each at a different distance from the reflective surface of the object.

6. A method as claimed in 5, wherein the recording device is moved to different positions along the optical axis of the reflected light to sequentially record the plurality of images.

7. A method as claimed in 5, comprising the further step of dividing the reflected light into a plurality of portions and directing each portion of the reflected light to a separate recording device in which the path length from the reflected surface of the object to each recording device is different.

8. A method as claimed in claim 7, wherein the effective path length of the reflected light is altered by adjustment of optical elements located between the object and the recording devices.

9. A method as claimed in claim 1, further comprising the step of modifying a beam of light and directing the modified beam to the reflective surface of the object by means of an adjustable optical system, wherein the adjustable optical system is changed between each image recording.

10. A method as claimed in claim 1, wherein the image generated by the reflected light is recorded at a plurality of different, distinct wavelengths.

11. Topographical analysis apparatus for measuring variations in the reflectivity or surface height of a reflective object comprising an optical system for directing a beam of light to a reflective surface of the object;
    a first recording device for recording a first image of the surface of the object generated by light reflected from the surface; at least one further recording device for recording one or more further images of the surface of the object, thereby generating a plurality of images in which each image has a predetermined optical transformation with respect to every other image; and an analyser for measuring the light intensity distribution in each of the plurality of images and for determining and outputting at least one of the reflectivity and the relative surface height of the reflective surface of the object by iteratively adjusting a theoretical surface, having an initial predetermined reflectivity and surface height, until the calculated light intensity distributions for the theoretical surface, corresponding to the optical transformations of each of the recorded images, converge with the recorded images.

12. Topographical analysis apparatus as claimed in claim 11, wherein the analyser further includes a thresholding device for monitoring the difference between the calculated image intensity of the theoretical surface and the recorded image intensities and for determining that the theoretical surface substantially corresponds to the surface of the reflective object when the difference is less than a predetermined value.

13. Topographical analysis apparatus as claimed in claim 11, wherein there is further provided a light source.

14. Topographical analysis apparatus as claimed in claim 13, wherein the light source has a narrow band-width.

15. Topographical analysis apparatus as claimed in claim 11, wherein the recording apparatus comprises a plurality of recording devices being electronic cameras.

16. Topographical analysis apparatus as claimed in claim 15, wherein the plurality of detector devices is wavelength specific and each is sensitive to a different distinct wavelength.

17. Topographical analysis apparatus as claimed in claim 16, further including a plurality of wavelength specific light sources.

18. Topographical analysis apparatus as claimed in any one of claims 11 to 15, further including one or more beam splitters for dividing the reflected light into a plurality of portions and for directing each portion to a different detector device.

19. Topographical analysis apparatus as claimed in claim 11, wherein the recording apparatus device is a single camera mounted on a moveable support for positioning the camera at different distances from the reflective surface of the object.

20. Topographical analysis apparatus as claimed in claim 11, wherein one or more adjustable optical elements are provided between the object and the recording apparatus, the optical elements being mounted on a movable support so as to alter the effective path length of the reflected light.

21. Topographical analysis apparatus as claimed in claim 11, wherein an adjustable optical system is provided between the light source and the object, one or more elements of the optical system being mounted on a moveable support so as to modify the illuminating beam of light.

22. A method of adjusting a Makyoh topograph to enable quantitative measurement of the surface of a reflective object comprising introducing plural imaging means for enabling one or more further Makyoh topograms to be detected each having a different optical transformation with respect to every other topogram; measuring the light intensity distribution in each of the topograms generated by the reflected light; and determining at least one of the reflectivity and the relative surface height of the reflective surface of the object by predicting the reflectivity and relative surface height of an initial theoretical surface, iteratively adjusting the theoretical surface until the theoretical light intensity distributions for the theoretical surface, corresponding to the optical transformations of each of the topograms, converge with the topograms.

* * * * *